US011654150B2

(12) United States Patent
Delaet et al.

(10) Patent No.: US 11,654,150 B2
(45) Date of Patent: May 23, 2023

(54) DARUNAVIR COMBINATION FORMULATIONS

(71) Applicants: Janssen Sciences Ireland Unlimited Company, County Cork (IE); Gilead Sciences, Inc., Foster City, CA (US)

(72) Inventors: Urbain Alfons C. Delaet, Balen (BE); Philip Erna H. Heyns, Vosselaar (BE); Eugeen Maria Jozef Jans, Meerhout (BE); Roel Jos M. Mertens, Balan (BE); Geert Van Der Avoort, Retie (BE)

(73) Assignee: Janssen Sciences Ireland UC, Little Island (IE)

( * ) Notice: Subject to any disclaimer, the term of this patent is extended or adjusted under 35 U.S.C. 154(b) by 222 days.

(21) Appl. No.: 16/697,888

(22) Filed: Nov. 27, 2019

(65) Prior Publication Data
US 2020/0093840 A1   Mar. 26, 2020

Related U.S. Application Data

(62) Division of application No. 14/131,282, filed as application No. PCT/EP2012/063249 on Jul. 6, 2012, now abandoned.

(30) Foreign Application Priority Data

Jul. 7, 2011   (EP) ..................................... 11173067

(51) Int. Cl.
| A61K 31/635 | (2006.01) |
| A61K 31/5377 | (2006.01) |
| A61K 9/28 | (2006.01) |
| A61K 9/20 | (2006.01) |
| A61K 9/16 | (2006.01) |

(52) U.S. Cl.
CPC .......... *A61K 31/635* (2013.01); *A61K 9/2009* (2013.01); *A61K 9/2054* (2013.01); *A61K 9/2095* (2013.01); *A61K 9/28* (2013.01); *A61K 31/5377* (2013.01); *A61K 9/1652* (2013.01)

(58) Field of Classification Search
CPC .. A61K 31/635; A61K 9/2009; A61K 9/2054; A61K 9/2095; A61K 9/28; A61K 31/5377; A61K 9/1652; A61P 31/18; A61P 31/00; A61P 37/04
See application file for complete search history.

(56) References Cited

U.S. PATENT DOCUMENTS

| 6,248,775 | B1 | 6/2001 | Vazquez |
| 7,700,645 | B2 | 4/2010 | Vermeersch |
| 2005/0119338 | A1 | 6/2005 | Van Der Geest |
| 2008/0039428 | A1 | 2/2008 | Allaway et al. |
| 2008/0113021 | A1 | 5/2008 | Shen |
| 2014/0037724 | A1 | 2/2014 | Dahl |
| 2014/0142070 | A1 | 5/2014 | Delaet et al. |
| 2014/0142174 | A1 | 5/2014 | Delaet et al. |
| 2016/0113949 | A1 | 4/2016 | Delaet et al. |

FOREIGN PATENT DOCUMENTS

| EP | 0715618 B1 | 12/1998 |
| EP | 2568810 B1 | 9/2018 |
| WO | WO1999/067417 A2 | 12/1999 |
| WO | WO2003/049746 A2 | 6/2003 |
| WO | WO2007/143422 A2 | 12/2007 |
| WO | WO2008/010921 A2 | 1/2008 |
| WO | WO2008/103949 A1 | 8/2008 |
| WO | WO2009/000853 A2 | 12/2008 |
| WO | WO2009/013356 A2 | 1/2009 |
| WO | WO2009/067401 A1 | 5/2009 |
| WO | WO2009/081174 A2 | 7/2009 |
| WO | WO2009/135179 A2 | 11/2009 |
| WO | WO2010/091197 A2 | 8/2010 |
| WO | WO2011/048604 A2 | 4/2011 |
| WO | WO2013/004816 A1 | 1/2013 |
| WO | WO2013/004818 A1 | 1/2013 |
| WO | 2013115916 A1 | 8/2013 |
| WO | 2016/108205 A1 | 7/2016 |

OTHER PUBLICATIONS

Xu, Cobicistat (GS-9350): A Potent and Selective Inhibitor of Human CYP3A as a Novel Pharmacoenhancer, ACS Med. Chem. Lett., 2010, 1, pp. 209-213 (Year: 2010).*
DOW (Methocel as a Granulation Binding Agent for Immediate-Release Tablet and Capsule Products, 2003, pp. 1-16).
DOW (Methocel Cellulose Ethers in Aqueous Systems for Tablet Coating, 2002, pp. 1-32).
Ghosh et al., "Potent HIV Protease inhibitors incorporating high-affinity P2-ligands and (R) (Hydroxyethylamino) Sulfonamide Isostere", Bioorganic and Chimistry Letters 8, (1998), pp. 687-690.
Handbook of Pharmaceutical Granulation Technology, 2 ed., edited by Dilip M. Parikh, 2005, pp. 113, 268-269.
Handbook of Pharmaceutical Excipients, 5. ed., edited by Raymond C. Rowe, Paul J. Sheskey, Siân C. Owen, 2006, pp. 346-349.
International Search Report and Written Opinion for International Application No. PCT/EP2012/063242, dated Aug. 6, 2012.
International Search Report and Written Opinion for International Application No. PCT/EP2012/063249, dated Oct. 1, 2012.
Karmarkar, A.B., Effect of Ceolus KG-802 on the dissolution rate of fenofibrate liquisolid tablets: Preformulation and formulation development studies, Drugs Discoveries & Therapeutics, 2010, 4(6), pp. 493-498.
Li, C.L. et al., The use of hypromellose in oral drug delivery, Journal of Pharmacy and Pharmacology, 2005, 57, pp. 533-546.

(Continued)

*Primary Examiner* — Savitha M Rao
*Assistant Examiner* — Andrew P Lee

(57) ABSTRACT

This invention relate to solid oral dosage forms of tire HIV inhibitor Darunavir and/or a pharmaceutically acceptable salt or solvate thereof, and combination formulation thereof.

12 Claims, No Drawings

(56) References Cited

OTHER PUBLICATIONS

Wensing, A.M. et al., "Fifteen years of HIV Protease Inhibitors: raising the barrier to resistance", Antiviral Research, Elsevier BV, NL, vol. 85, No. 1, pp. 59-74.
Birkus, et al., Activation of 9-[(R)-2-[[(S)-[[(S)-1-(Isopropoxycarbonyl)ethyl]amino] phenoxyphosphinyl]-methoxy] propyl]adenine (GS-7340) and Other Tenofovir Phosphonoamidate Prodrugs by Human Proteases, Molecular Pharmacology, Apr. 22, 2008, pp. 92-100, vol. 74 Issue 1.
Birkus, et al., Cathepsin A Is the Major Hydrolase Catalyzing the Intracellular Hydrolysis of the Antiretroviral Nucleotide Phosphonoamidate Prodrugs GS-7340 and GS-9131, Antimicrobial Agents and Chemotherapy, 2007, pp. 543-530, vol. 51 Issue 2.
Blum, et al., Steady-State Pharmacokinetics of Emtricitabine and Tenofovir Disoproxil Fumarate Administered Alone and in Combination in Healthy Volunteers, Journal of Clinical Pharmacology, Feb. 14, 2007, pp. 751-759, vol. 47.
Cahn, et al., Week 48 analysis of once-daily vs. twice-daily darunavir/ritonavir in treatment-experienced HIV-1-infected patients, AIDS, Feb. 18, 2011, pp. 929-939, vol. 25 Issue 7.
Chastain, D., et al., Optimizing Antiretroviral Therapy in Treatment-Experienced Patients Living with HIV: A Critical Review of Switch and Simplification Strategies. An Opinion of the HIV Practice and Research Network of the American College of Clinical Pharmacy, Journal of the International Association of Providers of AIDS Care, 2019, vol. 18/1-22, DOI: 10.1177/2325958219867325.
Clay, et al., Meta-Analysis of Studies Comparing Single and Multi-Tablet Fixed Dose Combination HIV Treatment Regimens, Medicine, Sep. 2, 2015, pp. 1-14, vol. 94 Issue 42.
ClinicalTrials.gov NCT02269917, Study to Evaluate Efficacy and Safety of Darunavir/Cobicistat/Emtricitabine/Tenofovir Alafenamide (D/C/F/TAF) Regimen Versus Boosted Protease Inhibitor (bPI) Along With Emtricitabine/Tenofovir Disoproxil Fumarate (FTC/TDF) Regimen in Virologically-Suppressed . . . , 2014, https://clinicaltrials.gov/ct2/show/NCT02269917?term=D%2FC%2FF%2FTAF&age=1&phase=2& draw=1 &rank=1.
ClinicalTrials.gov NCT02431247, A Study to Evaluate Efficacy and Safety of Darunavir/Cobicistat/Emtricitabine/Tenofovir Alafenamide (D/C/F/TAF) Fixed Dose Combination (FDC) Versus a Regimen Consisting of Darunavir/Cobicistat FDC With Emtricitabine/Tenofovir Disoproxil Fumarate FDC in . . . , 2015, https://clinicaltrials.gov/ct2/show/NCT02431247?term=D%2FC%2FF%2FTAF&age=1 &phase=2& draw=1 &rank=2.
ClinicalTrials.gov NCT02475135, Relative Bioavailability and Food Effect for Darunavir/Cobicistat/Emtricitabine/Tenofovir Alafenamide Fixed Dose Combination, 2015, https://clinicaltrials.gov/ct2/show/NCT02475135?term=NCT02475135&rank=1.
ClinicalTrials.gov NCT02578550, A Bioequivalence Study of Darunavir, Emtricitabine, and Tenofovir Alafenamide, in the Presence of Cobicistat in Healthy Participants, 2015, https://clinicaltrials.gov/ct2/show/NCT02578550?term=NCT02578550&rank=1.
ClinicalTrials.gov NCT03227861, A Study to Evaluate the Efficacy and Safety of (D/C/F/TAF) Once Daily Fixed Dose Combination (FDC) Regimen in Newly Diagnosed, Antiretroviral Treatment-naive Human Immunodeficiency Virus Type 1 (HIV-1) InfectedParticipants Receiving Care in a Test and Treat Model of Care, 2017, https://clinicaltrials.gov/ct2/show/NCT03227861?term=NCT03227861&rank=1.
Cockcroft, et al., Prediction of creatinine clearance from serum creatinine., Nephron, Jan. 28, 1975, pp. 31-41, vol. 16.
Crauwels, et al., Impact of food on the bioavailability of darunavir, cobicistat, emtricitabine and tenofovir alafenamide, the first protease inhibitor-based complete HIV-1 regimen (DCFTAF), J Acquir Immune Defic Syndr AIDS Patient Care STDS AIDS, 2016, Retrieved from the Internet: URL:http://programme.aids2016.org/PAGMaterial/eposters/0_3076.pdf.
Dejesus, et al., Simplification of Antiretroviral Therapy to a Single-Tablet Regimen Consisting of Efavirenz, Emtricitabine, and Tenofovir Disoproxil Fumarate Versus Unmodified Antiretroviral Therapy in Virologically Suppressed HIV-1-Infected Patients, J Acquir Immune Defic Syndr, Jun. 1, 2009, pp. 163-174, vol. 51 Issue 2.
Dimala, C.A., et al., Motives for change of first-line antiretroviral therapy regimens in an unselected cohort of HIV/AIDS patients at a major referral centre in South-west Cameroon, BMC Res Notes, 2017, 10:623; DOI 10.1186/s13104-017-2948-3.
Eron, et al., Week 48 results of AMBER: a phase 3, randomised, double-blind trial in antiretroviral treatment-naïve HIV-1-infected adults to evaluate the efficacy and safety of the once-daily, single-tablet regimen of darunavr/cobicistat/emtricitabine/tenofovir alafenamide (D/C/F/TAF) versus darunavir/cobicistat plus emtricitabine/tenofovir disoproxil fumarate, EACS, 2017, Abstract PS8/2.
Flynn, et al., Efficacy and Safety of Darunavir/Ritonavir at 48 Weeks in Treatment-naïve, HIV-1-infected Adolescents, The Pediatric Infectious Disease Journal, Feb. 5, 2014, pp. 940-945, vol. 33 Issue 9.
Golkowski, et al., Blinded sample size re-estimation in crossover bioequivalence trials, Pharmaceutical Statistics, Apr. 9, 2014, pp. 157-162, Volulme 13.
Hodder, et al., Patient-Reported Outcomes in Virologically Suppressed, HIV-1-Infected Subjects After Switching to a Simplified, Single-Tablet Regimen of Efavirenz, Emtricitabine, and Tenofovir DF, AIDS Patient Care and STDs, 2010, pp. 87-96, vol. 24 Issue 2.
Huhn, et al., "Darunavir/Cobicistat/Emtricitabine/Tenofovir Alafenamide in Rapid-Initiation Model of Care for Human Immunodeficiency Virus Type 1 Infection: Primary Analysis of the DIAMOND Study", Clinical Infectious Diseases, vol. 71 (12) : pp. 3110-3117 (2020).
Huhn, et al., "Darunavir/cobicistat/emtricitabine/tenofovir alafenamide in treatment-experienced, virologically suppressed patients with HIV-1: subgroup analyses of the phase 3 EMERALD study", AIDS Research and Therapy, vol. 16 (23), pp. 1-11 (2019).
Huhn, et al., "Darunavir/Cobicistat/emtricitabine/tenofovir alafenamide in treatment-experiences, virologically suppressed patitents with HIV-1: subgroup analyses of the phase 3 Emerald Study—Additional File", AIDS Res Ther, (Aug. 29, 2019), pp. 1-8, vol. 16 (23).
Huhn, et al., A Randomized, Open-Label Trial to Evaluate Switching to Elvitegravir/Cobicistat/Emtricitabine/Tenofovir Alafenamide Plus Darunavir in Treatment-Experienced HIV-1-infected Adults, Journal of Acquired Immune Deficiency Syndromes, Feb. 1, 2017, pp. 193-200, vol. 74 Issue 2.
International Search Report and Written Opinion dated Oct. 25, 2018, for International Application No. PCT/US2018/042937.
Johnson, et al., Update of the Drug Resistance Mutations in HIV-1: Dec. 2010, Topics in HIV Medicine, 2010, pp. 156-163, vol. 18, No. 5.
Kakuda, et al., Bioequivalence of a darunavir/cobicistat fixed-dose combination tablet versus single agents and food effect in healthy volunteers, Antiviral Therapy, 2014, pp. 597-606, vol. 19.
Kuo, et al., "Weight gain and dyslipidemia among virally suppressed HIV-positive patients switching to co-formulated elvitegravir/cobicistat/emtricitabine/tenofovir alafenamide", International Journal of Infectious Diseases, vol. 92: pp. 71-77 (2020).
Lee, et al., Selective Intracellular Activation of a Novel Prodrug of the Human Immunodeficiency Virus Reverse Transcriptase Inhibitor Tenofovir Leads to Preferential Distribution and Accumulation in Lymphatic Tissue, Antimicrobial Agents and Chemotherapy, 2005, pp. 1898-1906, vol. 49 Issue 5.
Meloni, S.T., et al., Implication of First-Line Antiretroviral Therapy Choice on Second-Line Options, Open Forum Infectious Diseases, 2017, DOI: 10.1093/ofid/ofx233.
Mills, et al., Once-daily darunavir/ritonavir vs. lopinavir/ritonavir in treatment-naive, HIV-1-infected patients: 96-week analysis, AIDS, Apr. 27, 2009, pp. 1679-1688, vol. 23 Issue 13.
Mills, et al., Tenofovir Alafenamide Versus Tenofovir Disoproxil Fumarate in the First Protease Inhibitor-Based Single-Tablet Regimen for Initial HIV-1 Therapy: A Randomized Phase 2 Study, Journal of Acquired Immune Deficiency Syndromes, Aug. 1, 2015, pp. 439-445, vol. 69 Issue 4.
Mussini, C., et al., Switching to dual/monotherapy determines an increase in CD8+ in HIV-infected individuals: an observational cohort study, BMC Medicine, 2018, 16:79; https://doi.org/10.1186/s12916-018-1046-2.

(56) References Cited

OTHER PUBLICATIONS

Niaid, Division of AIDS table for grading the severity of adult and pediatric adverse events—version 2. https://rsc.tech-res.com/docs/default-source/safety/daids_ae_grading _table_v2_nov2014.pdf?sfvrsn=8 (Nov. 2014; accessed Apr. 25, 2017).

Orwood MD, et al., "Weight Gain in Persons with HIV Switched from Efavirenz-based to Integrase Stand Transfer Inhibitor-Based Regimens", J Acquir Immune Defic Syndr, vol. 76 (5): pp. 527-531, (Dec. 15, 2017).

Orkin, et al., Efficacy and safety of switching from boosted protease inhibitors plus emtricitabine and tenofovir disoproxil fumarate regimens to single-tablet darunavir, cobicistat, emtricitabine, and tenofovir alafenamide at 48 weeks in adults with virologically suppressed HIV-1 (EMERALD): a phase 3, randomised, non-inferiority trial, (and Supplementary Appendix) Lancet HIV, 2017, pp. 1-169.

Orkin, et al., Final 192-week efficacy and safety of once-daily darunavir/ritonavir compared with lopinavir/ritonavir in HIV-1-infected treatment-naïve patients in the ARTEMIS trial*, HIV Medicine, 2013, pp. 49-59, Volulme 14.

Ortiz, et al., Efficacy and safety of once-daily darunavir/ritonavir versus lopinavir/ritonavir in treatment-naive HIV-1-infected patients at week 48, AIDS, Mar. 17, 2008, pp. 1389-1397, vol. 22 Issue 12.

Perrier, M., et al., Switch as maintenance to elvitegravir/cobicistat/emtricitabine/ tenofovir disoproxil fumarate: week 48 results in a clinical cohort, J Antimicrob Chemother, 2017, pp. 1745-1751, vol. 72.

Ruane, et al., Antiviral Activity, Safety, and Pharmacokinetics/Pharmacodynamics of Tenofovir Alafenamide as 10-Day Monotherapy in HIV-1-Positive Adults, J Acquir Immune Defic Syndr, Aug. 1, 2013, pp. 449-455, vol. 63 Issue 4.

Ruxrungtham, et al., Rationale and Clinical Utility of the darunavir-cobicistat combination in the treatment of HIV/AIDS, Drug Design Development and Therapy, 2015, pp. 5763-5769, vol. 9.

Sax, et al., Tenofovir Alafenamide Vs. Tenofovir Disoproxil Fumarate in Single Tablet Regimens for Initial HIV-1 Therapy: A Randomized Phase 2 Study, J Acquir Immune Defic Syndr, Sep. 1, 2014, pp. 52-58, vol. 67 Issue 1.

Sekar, et al., The Effect of Different Meal Types on the Pharmacokinetics of Darunavir (TMC114)/Ritonavir in HIV-Negative Healthy Volunteers, J Clin Pharmacol, 2007, pp. 479-484, vol. 47.

Shearer, K., et al., Treatment outcomes of over 1000 patients on second-line, protease inhibitor-based antiretroviral therapy from four public-sector HIV treatment facilities across Johannesburg, South Africa, Tropical Medicine and International Health, 2017, pp. 221-231, vol. 22, No. 2.

Tashima, et al., Cobicistat-boosted darunavir in HIV-1-infected adults: week 48 results of a Phase IIIb, open-label single-arm trial, AIDS Research and Therapy, 2014, pp. 1-12, vol. 11 Issue 39.

Willig, et al., Increased regimen durability in the era of once-daily fixed-dose combination antiretroviral therapy, AIDS, Jun. 27, 2008, pp. 1951-1960, vol. 22.

* cited by examiner

DARUNAVIR COMBINATION FORMULATIONS

CROSS REFERENCE TO RELATED APPLICATIONS

This application is a divisional of U.S. application Ser. No. 14/131,282, filed Jan. 7, 2014, which is the National Stage Entry of International Application No. PCT/EP2012/063249, filed Jul. 6, 2012, which claims the benefit of European Patent Application No. 11173067.7, filed Jul. 7, 2011, the entireties of which are incorporated by reference herein.

FIELD OF THE INVENTION

This invention relates to solid oral dosage forms of the HIV inhibitor darunavir and combination formulations thereof.

BACKGROUND OF THE INVENTION

The treatment of Human Immunodeficiency Virus (HIV) infection, known as cause of the acquired immunodeficiency syndrome (AIDS), remains a major medical challenge. HIV is able to evade immunological pressure, to adapt to a variety of cell types and growth conditions and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs) and the more recent fusion inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retroviral Therapy) resulted in a remarkable improvement in anti-HIV therapy, leading to a large reduction in HIV-associated morbidity and mortality. Current guidelines for antiretroviral therapy recommend such triple combination therapy regimen even for initial treatment. However, none of the currently available drug therapies is capable of completely eradicating HIV. Even HAART may face the emergence of resistance, often due to non-adherence and non-persistence with antiretroviral therapy. In these cases HAART can be made effective again by replacing one of its components by one of another class. If applied correctly, treatment with HAART combinations can suppress the virus for many years, up to decades, to a level where it no longer can cause the outbreak of AIDS.

Because of their pharmacokinetic properties and the need to keep plasma levels above a minimum level, currently used anti-HIV drugs require frequent administration of relatively high doses. The number and/or volume of dosage forms that need to be administered are commonly referred to as the "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this also leads to the emergence of viral resistance. The problems associated with a high pill burden are multiplied where a patient must take a combination of different anti-HIV agents or agents in combination with a so called booster to improve pharmacokinetic properties.

Providing high dosage forms that have a relatively small size contributes to the convenience of intake and therefore also helps to overcome problems of pill burden.

Therefore, it would be desirable to provide HIV inhibitory therapy dial reduces pill burden in that it involves the administration of dosage forms of a practical size and additionally does not require frequent dosing.

One class of HIV drugs that is used in HAART is that of the PIs amongst which is darunavir (TMC114), approved in the U.S., the E.U. and a number of other countries and available under the trade name Prezista™. Darunavir, currently marketed in the form of darunavir monoethanolate, has the following chemical name: [(1S,2R)-3-[[(4-aminophenyl)sulfonyl (2-methylpropyl)amino]-2-hydroxy-1-(phenylmethyl)-propyl]-carbamic acid (3R,3aS,6aR)-hexahydrofuro[2,3-b]furan-3-yl ester monoethanolate. Its molecular formula is $C_{27}H_{37}N_3O_7S \cdot C_2H_5OH$, with a molecular weight of 593.73, and the following chemical structure:

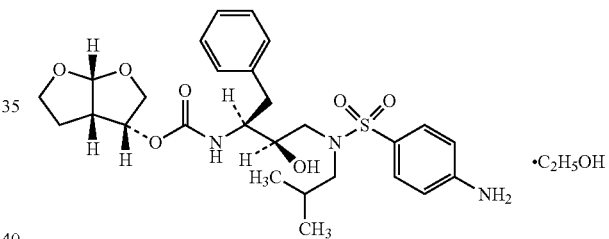

Darunavir as well as processes for its preparation are disclosed in EP 715618, WO99/67417, U.S. Pat. No. 6,248,775, and in Bioorganic and Chemistry Letters, Vol. 8, pp. 687-690, 1998, "Potent HIV protease inhibitors incorporating high-affinity $P_2$-ligands and (R) (hydroxyethylamino) sulfonamide isostere", all incorporated herein, by reference.

Improved combination formulations of darunavir with pharmacokinetic boosters, e.g. cytochrome $P_{450}$ inhibitors, are disclosed in WO03/049746.

An example of a suitable cytochrome $P_{450}$ inhibitor is GS-9350, also known under the name Cobicistat. GS-9350 is loaded on silicon dioxide, preferably colloidal silicon dioxide, and has the following chemical name: 12-methyl-13-[2-(1-methylethyl)-4-thiazolyl]-9-[2-(4-morpholinyl) ethyl]-8,11-dioxo-3,6-bis(phenylmethyl)-, 5-thiazolylmethyl ester, (3R,6R,9S)-. Its molecular formula is $C_{40}H_{53}N_7O_5S_2$, with a molecular weight of 776,023 g/mol, and the following chemical structure:

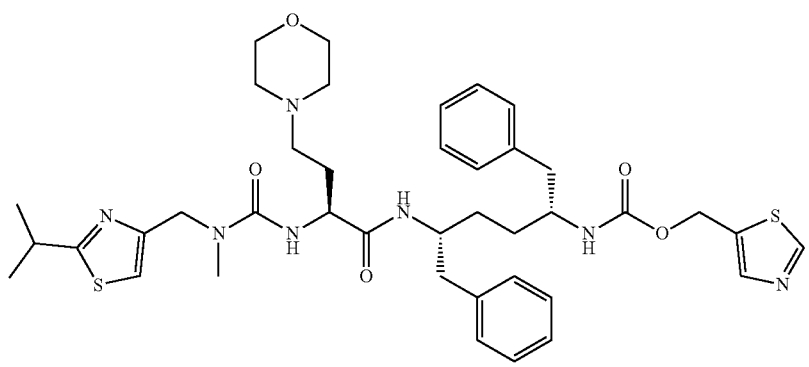 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

GS-9350 as well as processes for its preparation are disclosed in WO2008/010921, WO2008/103949 and WO2009/135179, all incorporated herein by reference.

Because high darunavir dosage forms are inevitably large in size, higher dose or combination dosage forms would take a size that surpasses the convenience barrier. In order to reduce pill-burden it would be desirable to achieve a dosage form with an increased weight % of darunavir per dosage form. This would facilitate either the generation of a higher dose tablet, or a reduction in size of the present dose tablets. It would be additionally desirable to combine darunavir, especially high dosages of darunavir, and a pharmacokinetic booster agent e.g. GS-9350 in one dosage form.

A darunavir tablet containing 600 mg of active ingredient and having a total weight of 1250 mg per tablet is disclosed in WO/2009/013356. The oral dosage forms are formed by direct compression of the ingredients.

Higher dose darunavir formulations, dose-proportionally derived from the currently marketed 600-mg tablet, were not deemed desirable for use by patients because of their large size.

Furthermore, the direct compression method led to inferior results when increasing the percentage of darunavir in the formulation. Inferior results are obtained due to limited gliding and flowing capacity of such a formulation. This is also the case when other actives are added to the formulation.

The present invention is based on the unexpected finding that a high weight % load of darunavir per dosage form is facilitated by the granulation of darunavir before formulation.

Granulation of darunavir according to the present invention thus facilitates a high loading of darunavir in a single dosage form (>80% (w/w)) or the combination of darunavir with other active ingredients and still having an acceptable size of the dosage form.

The present invention thus provides anti-HIV therapy involving the administration of darunavir dosage forms of acceptable size, potentially as a combination formulation, thereby requiring less frequent dosing. Hence, present dosage forms are beneficial in terms of pill burden and drug compliance of the patient.

SUMMARY OF THE INVENTION in one aspect the invention relates to an oral dosage form comprising about 0.4 to 0.6% by weight (w/w) of a lubricant, about 3% by weight (w/w) of a disintegrant, 17 to 20% by weight (w/w) of silicon dioxide, preferably colloidal silicon dioxide, loaded with GS-9350 corresponding to a total amount of about 150 mg free form equivalent of GS-9350 and about 50 to 60% by weight (w/w) of darunavir granulate, said darunavir granulate consisting of darunavir and/or a pharmaceutically acceptable salt or solvate thereof, Hypromellose and any residual water from the granulation.

Preferably, the Hypromellose is Hypromellose 2910 15 mPa·s.

In yet another aspect, the invention relates to a process for preparing an oral dosage form according to the invention comprising the steps of:

Providing granulated darunavir by, mixing water and Hypromellose, spraying this first mixture on a powder of darunavir and/or a pharmaceutically acceptable salt or solvate thereof, and drying the so obtained darunavir granulate Providing a second mixture comprising microcrystalline cellulose, silicon dioxide, preferably colloidal silicon dioxide loaded with GS-9350, a disintegrant, Adding granulated darunavir to the mixture and subsequent dry-blending Adding a lubricant and mixing until homogeneous, Compressing the mixture to provide the oral dosage form, said oral dosage form then being optionally film-coated.

In yet another aspect, the present invention relates to an oral dosage form according to the invention for use in medicine, more specifically for use in the treatment of HIV infections In yet another aspect, the invention relates to a method for the treatment of an HIV infection in a subject which comprises administering to the subject an effective amount of an oral dosage form according to the invention.

DESCRIPTION OF THE INVENTION

The present invention provides an oral dosage form of darunavir and GS-9350 that is manufactured by using a darunavir granulate.

By making use of this granulate, the weight percentage darunavir can be increased per dosage form, thus generating oral dosage forms with a high dose of free from equivalent of darunavir (e.g. 800 mg). Additionally, the size and weight of existing dosage forms (e.g. 400 or 600 mg) can be reduced by about 25%.

Advantageously, the solid oral dosage forms can comprise additional active ingredients such as pharmacokinetic boosters, e.g. GS-9350 and still be of an acceptable size. The size of the dosage forms of the invention, i.e. the total weight of the dosage forms, should be below a limit of convenience which is below the size at which a number of patients starts having difficulty taking in the dosage form. The total weight of the dosage forms of the invention preferably is below about 1700 mg, and in particular below about 1650 mg.

The oral dosage forms of the present invention preferably are tablets.

As used herein, the term "darunavir" is meant to comprise the base form, any pharmaceutically acceptable acid addition salt thereof, as well as any pharmaceutically acceptable solvate thereof. The pharmaceutically acceptable addition salts as mentioned hereinabove the therapeutically active non-toxic acid addition salt forms, which darunavir is able to form. In one embodiment the term "darunavir" is meant to comprise the base form, as well as any pharmaceutically acceptable solvate thereof.

The term pharmaceutically acceptable solvate comprises the hydrates and the solvent addition forms that darunavir can form. Examples of such forms are e.g. hydrates, alcoholates, e.g. methanolates, ethanolates and propanolates, and the like.

Particular solvates are the ethanolate, e.g. the monoethanolate.

As used herein the term "free-form equivalent" refers to that quantity of darunavir or GS-9350, whether present in free form (or base form), or as salt or solvate, that corresponds to a given quantity of free form darunavir or GS-9350. For example 650 mg of darunavir monoethanolate corresponds to 600 mg of free-form equivalent darunavir.

For application in adults, high quantities of the active ingredients may be used. In such instance, the dosage forms of the invention contain from about 500 to about 900 mg, in particular from about 600 mg to about 800 mg, for example about 800 mg, of free-form equivalent darunavir per unit of the dosage form.

The darunavir in the dosage forms of the invention is added to the formulation process in the form of a darunavir granulate composition consisting of Darunavir or a pharmaceutically acceptable salt or solvate thereof, Hypromellose and any residual water from the granulation.

Preferably, the Darunavir is present in the form of its ethanolate and the Hypromellose is Hypromellose 2910 15 mPa·s.

The amount of darunavir in the granulate composition may be in the range from about 95% to about 100%, in particular about 97% to about 99.9%, or about 98% to about 99%, by weight relative to the total weight of the granulate composition comprising darunavir and Hypromellose 2910 15 mPa·s. The granulate composition may additionally contain residual water that is not completely removed during processing.

The average particle size of the granulate is between 100 and 500 μm, more preferably from 150 to 400 μm and even more preferably about 300 μm.

As used herein, the term average particle size has its conventional meaning as known to the person skilled in the art and can be measured by art-known particle size measuring techniques such as, for example, sedimentation field flow fractionation, photon correlation spectroscopy, laser diffraction or disk centrifugation. The average particle sizes mentioned herein may be related to weight distributions of the particles. In that instance, by "an average particle size of about 150 μm" it is meant that at least 50% of the weight of the particles have a particle size of less than average of 150 μm, and the same applies to the other particle sizes mentioned. In a similar manner, the average particle sizes may be related to volume distributions of the particles but usually this will result in the same or about the same value for the average effective particle size.

Granulation of darunavir preferably is performed in a fluid-bed granulator. Preferably, darunavir is granulated by using Hypromellose. More preferably, Hypromellose 2910 15 mPa·s is used. According to the present invention, darunavir is granulated without any filler or other excipients before formulation of the tablet core.

Preferably, the oral dosage forms according to the present invention will comprise a pharmacokinetic booster such as a cytochrome $P_{450}$ inhibitor. A preferred example of a cytochrome $P_{450}$ inhibitor is GS-9350. GS-9350 is provided as loaded onsilicon dioxide, preferably colloidal silicon dioxide. A suitable process for the preparation of silicon dioxide, preferably colloidal silicon dioxide, loaded with GS-9350 is described in WO 2009/135179, as incorporated herein by reference. The dosage forms of the invention comprise about 150 mg of free-form equivalent GS-9350 per unit of the dosage form.

GS-9350 can be used in base form or as a pharmaceutically acceptable addition salt form, in particular as an acid addition salt form, or as a pharmaceutically acceptable solvate. The pharmaceutically acceptable addition salts are meant to comprise the therapeutically active non-toxic salt forms.

The weight/weight ratio darunavir:GS-9350 may vary, but in one embodiment it is in the range from about 10:1 to about 4:5, in particular said ratio may be about 5:1.

Oral dosage forms according to the present invention will preferably comprise pharmaceutically acceptable carriers and excipients. Such inactive ingredients are added to help hold the tablet together and give it strength, among others binders, fillers disintegrant glidants and lubricants.

A wide variety of binders may be used, some common ones including lactose, dibasic calcium phosphate, sucrose, corn (maize) starch, microcrystalline cellulose and modified cellulose (for example hydroxymethyl cellulose). Other such materials are silicon dioxide, titanium dioxide, alumina, talc, kaolin, powdered cellulose, as well as soluble materials such as mannitol, urea, sucrose, lactose, dextrose, sodium chloride, and sorbitol. Such agents may sometimes also be referred to as "fillers".

Microcrystalline cellulose that can be used comprises the Avicel™ series of products available from FMC BioPolymer, in particular Avicel PH 105® (20 μm), Avicel PH 101® (50 μm), Avicel PH 301® (50 μm);
the microcrystalline cellulose products available from JRS Pharma, in particular Vivapur® 105 (20 μm), Vivapur® 101 (50 μm), Emcocel® SP 15 (15 μm), Emcocel® 50M 105 (50 μm), Prosolv® SMCC 50 (50 μm);
the microcrystalline cellulose products available from DMV, in particular Pharmacel® 105 (20 μm), Pharmacel®101 (50 μm);
the microcrystalline cellulose products available from Blanver, in particular Tabulose (Microcel)® 101 (50 μm), Tabulose (Microcel)® 103 (50 μm) the microcrystalline cellulose products available from Asahi Kasei Corporation, such as Ceolus® PH-F20JP (20 μm), Ceolus® PH-101 (50 μm), Ceolus® PH-301 (50 μm), Ceolus® KG-802 (50 μm).

A particularly preferred microcrystalline cellulose is Ceolus® KG-802, average particle size (50 μm). Additional characteristics of Ceolus® KG-802 are a bulk density of about 0.2($g/cm^3$) and an angle of repose of about 490.

The average particle size of the Microcrystalline cellulose may be in the range of from 5 μm to 60 μm, in particular from 10 μm to 50 μm, e.g. about 20 μm.

In addition to the presence of any of the above indicated ingredients, the tablet formulation according to the invention contains a lubricant. This provides a formulation which avoids manufacturing problems such as tablet sticking when the drug product blend is compressed into tablets.

The lubricant is preferably magnesium stearate and is generally present in an amount of 0.4 to 0.6% w/w, particularly about 0.5% w/w.

The tablet formulation also contains a disintegrant to aid disintegration and dissolution of the formulation upon administration to the patients. The preferred disintegrant is crospovidone, namely a synthetic homopolymer of cross-linked N-vinyl-2-pyrrolidone available commercially as Polyplasdone XL-10 and is preferably present in an amount of 1 to 4% w/w, especially about 3% w/w. Other disintegrants which may be used include croscarmellose sodium (sodium salt of cross-linked carboxymethylcellulose), available commercially as Acdisol.

The above tablet formulations can be used to make tablet cores in conventional manner for example by initially dry blending the ingredients, that preferably having been sieved. Subsequently, the lubricant is added to the dry-blended mixture for final dry-blending of the total tablet core blend, which is then compressed into tablets having the desired size and weight.

For taste-masking and cosmetic reasons the tablet cores according to the invention are generally provided with a film coating for example an Opadry film-coating, which is generally used in an amount of about 4% w/w based on the tablet core. Different coloring agents may be used in the film coating in order to differentiate between tablet strengths.

The coating can be applied to the core in coating suspension for example in purified water, followed by drying of the coated cores.

The administration of a dosage form in accordance with the present invention may suffice to treat HIV infection although it may be recommendable to co-administer other HIV inhibitors. The latter preferably include HIV inhibitors of other classes, in particular an NRTI, or NNRTI, but also a fusion inhibitor can be added. HIV inhibitors that may be co-administered by preference are those used in HAART combinations.

In certain instances, the treatment of HIV infection may be limited to only the dosage form of the invention, without co-administration of further HIV inhibitors. This option may be recommended, for example, where the viral load is relatively low, e.g. where the viral load (represented as the number of copies of viral RNA in a specified volume of serum) is below about 200 copies/ml, in particular below about 100 copies/ml, more in particular below 50 copies/ml, specifically below the detection limit of the virus. This type of monotherapy may be applied after initial treatment with a combination, of HIV drugs, such as any of the HAART combinations during a certain period of time until the viral load in blood plasma reaches the afore mentioned low viral level.

In a further aspect the present invention relates to the use of a dosage form in accordance with the invention, for the manufacture of a medicament for maintenance therapy of a subject infected with HIV. The present invention also relates to the use of a dosage form in accordance with the invention, for the manufacture of a medicament for treating a subject infected with HIV, wherein the dosage form is combined with two different NRTIs or NNRTIs.

As used herein the term "treatment of HIV infection" relates to a situation of the treatment of a subject being infected with HIV. The term "subject" in particular relates to a human being.

The doses of darunavir and GS-9350 in the dosage forms of the invention are selected so as to keep the blood plasma concentration of darunavir above the minimum blood plasma level between two administrations. The term "minimum blood plasma level" in this context refers to the lowest efficacious blood plasma level, the latter being that blood plasma level of active that provides effective treatment of HIV. The plasma levels of anti-HIV compounds should be kept above these threshold blood plasma levels because at lower levels the drugs may no longer be effective thereby increasing the risk of mutations.

The dosage forms of the present invention provide effective treatment of HIV infection in that the viral load is reduced while keeping viral replication suppressed. The limited number of drug administrations adds to the patients' compliance with the prescribed therapy.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value±10%, or ±5%, or ±2%, or ±1%. All documents cited herein are incorporated by reference in their entirety.

Examples

General

Excipients used throughout the examples are listed in Table 1.

TABLE 1

| Excipients | |
| --- | --- |
| Excipient | Reference name |
| PROSOLV ® SMCC HD90 | HD90 |
| Hypromellose 2910 15 mPa · s | Methocel E15LV premium |
| Colloidal Anhydrous Silica[a] | Cab-O-Sil M5P[b] |
| Crospovidone | Polyplasdone XL-10 |
| Magnesium Stearate | Vegetal, type 5712 |
| Coating powder brick red | Opadry II brick red 85F250001 |

[a]Colloidal Anhydrous Silica is alternately known as Colloidal Silicon Dioxide
[b]Alternative is Aerosil 200 from Degussa The film coating, combined with debossing and differences in tablet size, aids in the differentiation of the tablet strengths. A secondary function of the film coating is taste masking.

The excipients used in Opadry II red 85F250001 are listed in Table 2.

TABLE 2

| Composition for Coating powder brick red (Opadry II red 85F250001) | |
| --- | --- |
| Component | Composition (w/w) |
| Polyvinyl alcohol | 40.00 |
| Polyethylylene glycol 3350 | 20.20 |
| Talc | 14.80 |
| Titanium dioxide | 3.26 |
| Iron Oxide Red | 20.01 |
| Iron Oxide Yellow | 1.21 |
| Iron Oxide Black | 0.52 |

Example 1: Darunavir Granulation

1: Granulation

A high dose formulation, e.g. 800-mg darunavir formulation, dose-proportionally derived from the currently marketed 600-mg tablet, was not perceived as suitable for use by patients because of its large size. Furthermore, direct compression of an 800 mg formulation proved not possible due to severely limited gliding and flowing capacity. The formulations studied are shown in Table 3.

TABLE 3

Formulations used in concept feasibility testing

|  | A | | B | | C | |
|---|---|---|---|---|---|---|
| Ingredients | mg/tab | % | mg/tab | % | mg/tab | % |
| darunavir | 867.28 | 69.38 | 867.28 | 72.27 | 867.28 | 72.27 |
| MCC[a] | — | — | 287.12 | 23.93 | — | — |
| HPMC 2910 15 mPa · s | — | — | — | — | 24.00 | 2.00 |
| Purified water[b] | — | — | 1043 μl | — | 600 μl | — |
| Prosolv HD90 | 337.08 | 26.97 | — | — | 266.72 | 22.23 |
| Crospolyvidone | 25.01 | 2.00 | 36.00 | 3.00 | 36.00 | 3.00 |
| Colloidal anhydrous silica | 11.38 | 0.91 | 3.60 | 0.30 | — | — |
| Magnesium stearate | 9.25 | 0.74 | 6.00 | 0.50 | 6.00 | 0.50 |
| Total | 1250 | 100 | 1200 | 100 | 1200 | 100 |

[a]MCC = Microcrystalline Cellulose (Avicel PH101)
[b]Purified water does not appear in the final product Direct Compression Formulation A:

All ingredients, except magnesium stearate, were sieved over a stainless steel screen of 0.95 mm and blended for 10 minutes using a lab-scale planetary mixer. In a second blending step, the magnesium stearate was sieved and mixed for 5 minutes. The blend was not compressed, because of the bad flowability (angle of repose).

Wet Granulation Formulation B:

The powders of the internal phase (API/MCC) were sieved over a stainless steel screen with 0.95 mm sieve openings and transferred into the granulation insert of the fluid bed granulator GPCG1.

The purified water (without binder) was sprayed on the powder mixture. The process conditions for the granulation are reported in the table below.

TABLE 4

Granulation conditions (B)

|  | Mixing/heating | Granulation | Drying |
|---|---|---|---|
| Air flow | 63 > 64 m³/h | 64 <> 112 m³/h | 108 > 65 m³/h |
| Spray rate | — | 13 –> 23 g/min. | — |
| Atomizing air flow | 1.0 bar | 1.0 bar | 1.0 bar |
| Inlet air temperature | 60° C. (set) | 45° C. (set) 60 > 45° C. (actual) | 60 > 70° C. (set) 45 <> 77° C. (actual) |
| Outlet air temperature | 24 > 30° C. | 29 > 24° C. | 23 > 38° C. |

The dried granules and the excipients of the external phase were sieved (0.95 mm) and blended for 10 min. In a second step, the magnesium stearate was sieved, added and blended for 5 min. The granulate after sieving was tested for granulometrics and LOD.

This final mixture was compressed at different compression forces (750→2000 kg), using a single punch tablet press. The obtained tablets (nom. weight 1200 mg, punch AC27/42: 20 mm×9.5 mm, radius 3 mm, oblong shape) were analyzed for hardness, disintegration time and dissolution.

Wet Granulation Formulation C:

The API was sieved over a stainless steel screen with 0.95 mm sieve openings and transferred into the granulation insert of the fluid bed granulator GPCG1.

The binder solution (HPMC 15 cps 4% solution in water) was sprayed on the powder mixture. The process conditions for the granulation are reported in the table below.

TABLE 5

Granulation conditions GPCG1 (C)

|  | Mixing/heating | Granulation | Drying |
|---|---|---|---|
| Air flow | 60 m³/h | 60 <> 113 m³/h | 93 > 90 m³/h |
| Spray rate | — | 20 g/min | — |
| Atomizing air flow | 1.0 bar | 1.0 bar | 1.0 bar |
| Inlet air temperature | 60° C. (set) | 45 <> 55° C. (set) 51 <> 56° C. (actual) | 60° C. (set) 57 <> 68° C. (actual) |
| Outlet air temperature | 24 > 31° C. | 31 > 24° C. | 25 > 38° C. |

The dried granules and the excipients of the external phase were sieved (0.95 mm) and blended for 10 min. In a second step, the magnesium stearate was sieved, added and blended for 5 min.

Tablet characteristics of the compression mixtures (B and C are shown in Table 6. The Direct Compression concept A was not compressed, because of insufficient flowability (high angle of repose) of the blend. Tablet hardness was measured according to industry standard.

TABLE 6

Compression data and tablet characteristics

|  | Comp. force | | | | | |
|---|---|---|---|---|---|---|
|  | 750 kg | 1000 kg | 1250 kg | 1500 kg | 1750 kg | 2000 kg |
| B | | | | | | |
| Blend Flow Aspect | Tendency towards rat holding in hopper | | | | | |
| Aspect | Tablet splitting - lack of binding | | | | | OK |
| Hardness - daN | NE[1] | | | | | 18.0 |
| Disint. time - sec | NE | | | | | 134 |
| C | | | | | | |
| Blend Flow | Good flow (out of hopper) | | | | | |
| Aspect | OK (no defects) | | | | | |
| Hardness - daN | 8.8 | 11.9 | 14.6 | 15.6 | 19.4 | 19.0 |
| Disint. time - ''' | 2'11" | 3'13" | 6'18" | 15'34" | 21'29" | 23'23" |

[1]NE = not executed

Concept (C), in which the darunavir is granulated solely with an aqueous HPMC 15 mPa·s binder solution and Prosolv HD90 filler material is added extra-granularly (i.e., in the final dry mixture), provided a superior process.

2: Darunavir 800 mg Representative Formulation

Based on the superior process including granulation, a representative oral dosage form comprising 800 mg free from equivalent of darunavir was formulated. The qualitative and quantitative composition of such a representative oral dosage form is provided in Table 7.

TABLE 7

Representative darunavir (TMC114) 800-mg Tablet

| Component | 800 mg (mg/tablet) | (% wt) |
|---|---|---|
| Core Tablet | | |
| darunavir Ethanolate | 867.28[a] | 78.84 |
| Hypromellose 2910 15 mPa · s | 13.20 | 1.20 |
| Purified water[b] | 330.00 μL | 0.00 |
| Silicified Mycrocrystalline Cellulose[c] | 177.72 | 16.16 |
| Crospovidone | 33.00 | 3.00 |
| Colloidal Anhydrous Silica | 3.30 | 0.30 |
| Magnesium Stearate | 5.50 | 0.50 |
| Core Tablet Weight | 1100.00 | 100.00 |
| Film Coating | | |
| Coating powder brick red | 44.00 | 4.00 |
| Purified Water[b] | 176.00 μL | 0.00 |
| Total Tablet Weight | 1144.00 | 104.00 |

[a]Quantity of darunavir ethanolate equivalent to 800 mg of darunavir.
[b]Purified Water does not appear in the final product.
[c]A commercially available ('Prosolv HD90'), spray-dried mixture consisting of 98% (w/w) microcrystalline cellulose and 2% (w/w) colloidal silicon dioxide, individually meeting compendial requirements.

3: Large Scale Manufacturing Process According to the Present Invention

Several large scale badges were produced according to the specifications below.

Preparation of the 4% Binder Solution:

⅓ of total quantity of purified water was warm up until 75-85'C.

Hypromcllose 2910 15 mPa·s was added while mixing with strong vortex.

After mixing for 10-20 min, the rest of (cold) purified water was added, while mixing with vortex for 5-10 minutes. The creation of foam was avoided by pouring the water slowly along the wall of the vessel.

The solution was cooled and de-aerated until is clear and the temperature was = or <30° C.

Gentle mixing was applied for 1-2 min before the start of the granulation.

Wet Granulation Conditions (on GPCG-30 Granulator)

Darunavir was transferred into the granulation insert of the fluid bed granulator GPCG-30 and pro-warmed. The binder solution (HPMC 15 cps 4% solution in water) was sprayed on the powder mixture and finally the granulate was dried. The GPCG-30 fluid-bed parameters used for the batches granulated at target, dry and wet condition, respectively, are listed in the tables below.

TABLE 8

Granulation conditions on GPCG-30, target condition, D

| | Pre-warming | Granulation | Drying |
|---|---|---|---|
| Air flow | 500 m³/h | 700 > 950 m³/h | 950 > 700 m³/h |
| Spray rate | — | 200 > 250 g/min | — |
| Atomizing air flow | — | 3.2 bar | — |
| Inlet air temperature | 60° C. | 50° C. | 60° C. |
| Outlet air temperature | 36° C. (end) | 24.3° C. (end) | 37° C. (end) |

TABLE 9

Granulation conditions on GPCG-30, target condition, E

| | Pre-warming | Granulation | Drying |
|---|---|---|---|
| Air flow | 500 m³/h | 700 > 950 m³/h | 950 > 700 m³/h |
| Spray rate | — | 200 > 250 g/min | — |
| Atomizing air flow | — | 3.2 bar | — |
| Inlet air temperature | 60° C. | 50° C. | 65° C. |
| Outlet air temperature | 36° C. (end) | 24.9° C. (end) | 37° C. (end) |

TABLE 10

Granulation conditions on GPCG-30, dry consition, F

| | Pre-warming | Granulation | Drying |
|---|---|---|---|
| Air flow | 500 m³/h | 700 > 800 m³/h | 800 m³/h |
| Spray rate | — | 180 g/min | — |
| Atomizing air flow | — | 3.2 bar | — |
| Inlet air temperature | 60° C. | 55° C. | 65° C. |
| Outlet air temperature | 36° C. (end) | 25.7° C. (end) | 37° C. (end) |

TABLE 11

Granulation conditions on GPCG-30, wet condition, G

| | Pre-warming | Granulation | Drying |
|---|---|---|---|
| Air flow | 500 m³/h | 750 > 1300 m³/h | 1050 > 850 m³/h |
| Spray rate | — | 220 g/min | — |
| Atomizing air flow | — | 3.2 bar | — |
| Inlet air temperature | 55° C. | 45° C. | 65° C. |
| Outlet air temperature | 35° C. (end) | 22.6° C. (end) | 37° C. (end) |

Blending and Compression Conditions

The dried granules were sieved through a hand sieve size with 0.95 mm openings and subsequently blended with external phase excipients (sieved through to 0.95 mm hand sieve) in a Gallay bin blender for 10 min at 9 rpm. In a second step, the magnesium stearate was sieved, added and blended for 5 min.

Physical characteristics of the granulates and the final blends (compression mixtures) are listed in the tables below.

TABLE 12

Physical characteristics of the granulate

| | D target cond. | | E target cond. | F dry cond. | G wet cond. |
|---|---|---|---|---|---|
| | before sieving | after sieving | before sieving | before sieving | before sieving |
| Loose bulk volume (ml/g) | 2.16 | 2.18 | 2.20 | 2.24 | 2.08 |
| Tapped bulk volume (ml/g) | 1.98 | 1.98 | 1.99 | 2.00 | 1.91 |
| Hausner index | 1.09 | 1.10 | 1.11 | 1.12 | 1.09 |
| Carr index | 8.33 | 9.17 | 9.55 | 10.71 | 8.17 |
| Angle of repose | 37°40' | 39°30' | 39°40' | 44°20' | 36°40' |
| d50 (μ) | 318 | 313 | 302 | 265 | 393 |

TABLE 12-continued

Physical characteristics of the granulate

| | D target cond. | | E target cond. | F dry cond. | G wet cond. |
|---|---|---|---|---|---|
| | before sieving | after sieving | before sieving | before sieving | before sieving |
| d84 (μ) | 184 | 198 | 196 | 162 | 256 |
| d84/d50 | 0.58 | 0.63 | 0.65 | 0.61 | 0.65 |
| Fraction <75μ (%) | 0.4 | 0.2 | 0.2 | 0.2 | 0.0 |

TABLE 13

Physical characteristics of the final blend

| | D target cond. formula w/o aerosil | E target cond. final formula | F dry cond. final formula | G wet cond. final formula |
|---|---|---|---|---|
| Loose bulk volume (ml/g) | 2.06 | 2.08 | 2.11 | 1.98 |
| Tapped bulk volume (ml/g) | 1.80 | 1.84 | 1.88 | 1.78 |
| Hausner index | 1.14 | 1.13 | 1.12 | 1.11 |
| Carr index | 12.62 | 11.54 | 10.90 | 10.10 |
| Angle of repose | 43°20' | 36°20' (36°50')[1] | 37°40' | 35°40' |
| d50 (μ) | 318 | 263 | 244 | 332 |
| 484 (μ) | 179 | 146 | 139 | 198 |
| d84/d50 | 0.56 | 0.55 | 0.57 | 0.60 |
| Fraction <75μ (%) | 3.9 | 5.9 | 6.8 | 5.4 |

Compression Results

The final blend of the batches was compressed at nominal weight (1100 mg) at different compression forces and speeds on a Courtoy module S high-speed rotary tablet press (10-16 punches) using a demo punch (oval shape) set with dimension 19×9.5 mm. The obtained tablets were analyzed for weight, hardness, thickness, aspect, disintegration time and friability. During compression the compression settings, incl. ejection force were monitored.

The tablet cores compressed at target compression force (13N) were also coated on a lab-scale coater according to the final formulation composition (with Opadry II red at 4% level).

Despite the reasonably broad variation in GPCG-30 fluid-bed granulation conditions used, acceptable physical characteristics of the granulate and final blends are obtained in all cases (tables 12 and 13). As expected, a finer and less dense granulate is obtained when dryer thermodynamic conditions are used. Blend flowability improves with the addition of aerosil [(37°40' vs 43° 20' for batches E (with aerosil) and batches D (without aerosil), respectively], confirming the functionality of the aerosil glidant material. The addition of the external phase excipients has a beneficial effect on material flowability.

Very similar physical characteristics are obtained for the granulates of batches D and E manufactured under (almost) identical granulation conditions, confirming the reproducibility of the fluid-bed granulation process.

Drying of the granulate until an outlet-air temperature of 37° C. is reached results in a narrow LOD result range within 5.2 to 6.0% for the granulate and within 5.6 to 6.1% for the final blend, confirming the reproducibility of the drying process regardless of the granulation (thermodynamic) condition used.

Example 2: Darunavir GS-9350 Co-Formulation 2.1 Preparation of Darunavir Granulate A binder solution was prepared analogous to wet granulation form C.

The quantitative and qualitative composition of 1000 mg representative darunavir granulate as obtained by the described process is provided in Table 14.

TABLE 14

Quantitative and Qualitative Composition of darunavir granules

| Component | Quantity (mg) |
|---|---|
| darunavir ethanolate | 985.00 |
| Hypromellose 2910 15 mPa · s | 15.00 |
| Purified water[a] | 374.79 |
| Total | 1,000 |

[a]Removed during processing 2.2 Oral Dosage Forms Comprising Darunavir and GS-9350

2.2.1 For darunavir/GS-9350 eq. 800/150-mg oral film coated tablets (I);

1. 14.97 kg of the dried darunavir granules was sieved through an appropriate screen together with 4.896 kg GS-9350 loaded on colloidal silicon dioxide, 2.846 kg silicified microcrystalline cellulose, 1.897 kg microcrystalline cellulose and 765 g crospovidone
2. Mixture was collected in a suitable blender and mixed until hormgeneous
3. 127.5 g of magnesium stearate was sieved through an appropriate screen and add to the content of the blender
4. Mixed until homogeneous
5. Compressed into tablets on a suitable tablets press 2.2.2 for Darunavir/GS-9350 Eq. 800/150-Mg Oral Film Coated Tablets (II):

1. 14.09 kg of the dried darunavir granules was sieved through an appropriate screen together with 4.608 kg GS-9350 loaded on colloidal silicon dioxide, 6.008 kg silicified microcrystalline cellulose and 768 g crospovidone
2. Mixture was collected in a suitable blender and mix until homogeneous
3. 128 g of the magnesium stearate was sieved through an appropriate screen and add to the content of the blender
4. Mixed until homogeneous
5. Compressed into tablets on a suitable tablets press 2.3 Coating The tablet cores were transferred into a suitable coating apparatus where the tablet cores were warmed up by supplying warm air. Subsequently the spraying of a coating suspension on the tablets was started and the coated tabled were dried in the coating apparatus.

2.4. Rests 2.4.1

The quantitative and qualitative composition of 800/150-mg oral film coated tablet (I) is provided in Table 15.

TABLE 15

Quantitative and Qualitative Composition of the 800/150-mg oral film coated tablets (I)

| Component | Quantity per tablet (mg) |
| --- | --- |
| GS-9350 loaded on colloidal silicon dioxide | 288.00 |
| darunavir 908.6 mg/g granules | 880.48 |
| Silicified microcrystalline cellulose | 167.41 |
| Microcrystalline cellulose (Ceolus KG802) | 111.61 |
| Crospovidone | 45.00 |
| Magnesium stearate$^a$ | 7.50 |
| Core tablet weight | 1500.00 |
| Film coating | |
| Coating powder white | 45.00 |
| Purified water$^b$ | 180.00 |
| Total tablet weight | 1545.00 |

$^a$Vegetable grade
$^b$Removed during processing 2.4.2

The quantitative and qualitative composition of 800/150-mg oral film coated tablet (II) is provided in Table 16.

TABLE 16

Quantitative and Qualitative Composition of 800/150-mg oral film coated tablets (II)

| Component | Quantity per tablet (mg) |
| --- | --- |
| GS-9350 loaded on colloidal silicon dioxide | 288.00 |
| darunavir 908.6 mg/g granules | 880.48 |
| Silicified microcrystalline cellulose | 375.52 |
| Crospovidone | 48.00 |
| Magnesium stearate$^a$ | 8.00 |
| Core tablet weight | 1600.00 |
| Film coating | |
| Coating powder white | 48.00 |
| Purified water$^b$ | 192.00 |
| Total tablet weight | 1648.00 |

$^a$Vegetable grade
$^b$Removed during processing

As can be observed, the addition of Microcrystalline cellulose (Keolus KG802) even further reduces the oral dosage form weight.

The invention claimed is:

1. A process for preparing an oral dosage form comprising the steps of:
    (a) providing a dried darunavir granulate consisting of:
        (a) darunavir, and/or a pharmaceutically acceptable salt or solvate thereof,
        (b) hypromellose, and
        (c) water,
    wherein the dried darunavir granulate is prepared by: (i) mixing water and hypromellose to form a first mixture, (ii) spraying the first mixture on a powder of darunavir and/or a pharmaceutically acceptable salt or solvate thereof, to form a wet darunavir granulate, and (iii) drying the wet darunavir granulate to produce the dried darunavir granulate, wherein the darunavir or pharmaceutically acceptable salt or solvate thereof is about 95% to about 99.9%, by weight relative to the total weight of the dried darunavir granulate;
    (b) providing a second mixture comprising microcrystalline cellulose, silicon dioxide loaded with GS-9350, and a disintegrant;
    (c) adding the dried darunavir granulate of step (a) to the second mixture of step (b) and dry-blending to form a blend;
    (d) adding a lubricant to the blend and mixing to prepare a homogeneous mixture; and
    (e) compressing the homogenous mixture to produce the oral dosage form.

2. The process of claim 1, further comprising film-coating the oral dosage form.

3. The process of claim 1, wherein the hypromellose is hypromellose 2910 15 Mpa·s.

4. The process of claim 1, wherein the silicon dioxide loaded with GS-9350 is colloidal silicon dioxide loaded with GS-9350.

5. The process of claim 1, wherein the oral dosage form includes free form equivalent of darunavir of from 400 mg to about 800 mg.

6. The process of claim 1, wherein the average particle size of the darunavir granulate is between 100 μm and 500 μm.

7. The process of claim 1, wherein the average particle size of the darunavir granulate is between 150 μm and 400 μm.

8. The process of claim 1, wherein the average particle size of the darunavir granulate is about 300 μm.

9. The process of claim 1, wherein the weight:weight ratio of darunavir:GS-9350 is in the range of from about 10:1 to about 4:5.

10. The process of claim 1, wherein the weight:weight ratio of darunavir:GS-9350 is about 5:1.

11. The process of claim 1, wherein the lubricant is magnesium stearate.

12. The process of claim 1, wherein the disintegrant is crospovidone.

* * * * *